(12) United States Patent
Danforth

(10) Patent No.: US 12,409,057 B1
(45) Date of Patent: Sep. 9, 2025

(54) KNEE BRACE SPRING LOCK AND RELEASE HINGE

(71) Applicant: Michael Danforth, Ft. Pierce, FL (US)

(72) Inventor: Michael Danforth, Ft. Pierce, FL (US)

(\*) Notice: Subject to any disclaimer, the term of this patent is extended or adjusted under 35 U.S.C. 154(b) by 0 days.

(21) Appl. No.: 19/204,487

(22) Filed: May 10, 2025

(51) Int. Cl.
*A61F 5/01* (2006.01)

(52) U.S. Cl.
CPC .... *A61F 5/0123* (2013.01); *A61F 2005/0162* (2013.01); *A61F 2005/0165* (2013.01); *A61F 2005/0179* (2013.01)

(58) Field of Classification Search
CPC ............ A61F 5/0123; A61F 5/0125; A61F 2005/0158; A61F 2005/0162; A61F 2005/0165; A61F 2005/0179; B25J 9/0006
USPC ............................................. 602/16
See application file for complete search history.

(56) References Cited

U.S. PATENT DOCUMENTS

| | | | |
|---|---|---|---|
| 5,547,464 A | 8/1996 | Luttrell | |
| 5,749,840 A | 5/1998 | Mitchell | |
| 5,899,869 A * | 5/1999 | Barrack, Jr. | A61F 5/0125 602/16 |
| 6,635,024 B2 * | 10/2003 | Hatton | A61F 5/0125 602/26 |
| 7,553,289 B2 | 6/2009 | Cadichon | |
| 10,682,249 B2 | 6/2020 | Kazerooni | |
| 11,369,494 B2 | 6/2022 | Kazerooni | |
| 2009/0299244 A1 | 12/2009 | Chiang | |
| 2014/0005584 A1 | 1/2014 | Pretz | |
| 2015/0150708 A1 * | 6/2015 | Paez | A61F 5/0123 602/16 |
| 2017/0281390 A1 * | 10/2017 | Abdul-Hafiz | A61F 5/0125 |
| 2020/0383814 A1 * | 12/2020 | Vogel | A61F 5/0125 |
| 2023/0172741 A1 | 6/2023 | Johnson | |

* cited by examiner

*Primary Examiner* — Rachael E Bredefeld
*Assistant Examiner* — Seth R. Brown
(74) *Attorney, Agent, or Firm* — Bullock Law; Stephen Bullock

(57) ABSTRACT

A knee brace spring lock and release hinge including a first section and second section. The first section has an arched support housing with a J-curved recess. The second section includes a base with base platform, an arched support surrounding a rotational wheel, a wheel pad abutting a portion of the wheel, and at least one spring extending from the base platform to the wheel pad. The second section is structured to rotate within the J-curved recess when the at least one spring is extended. The second section is structured to be locked into place when the at least one spring is compressed.

20 Claims, 8 Drawing Sheets

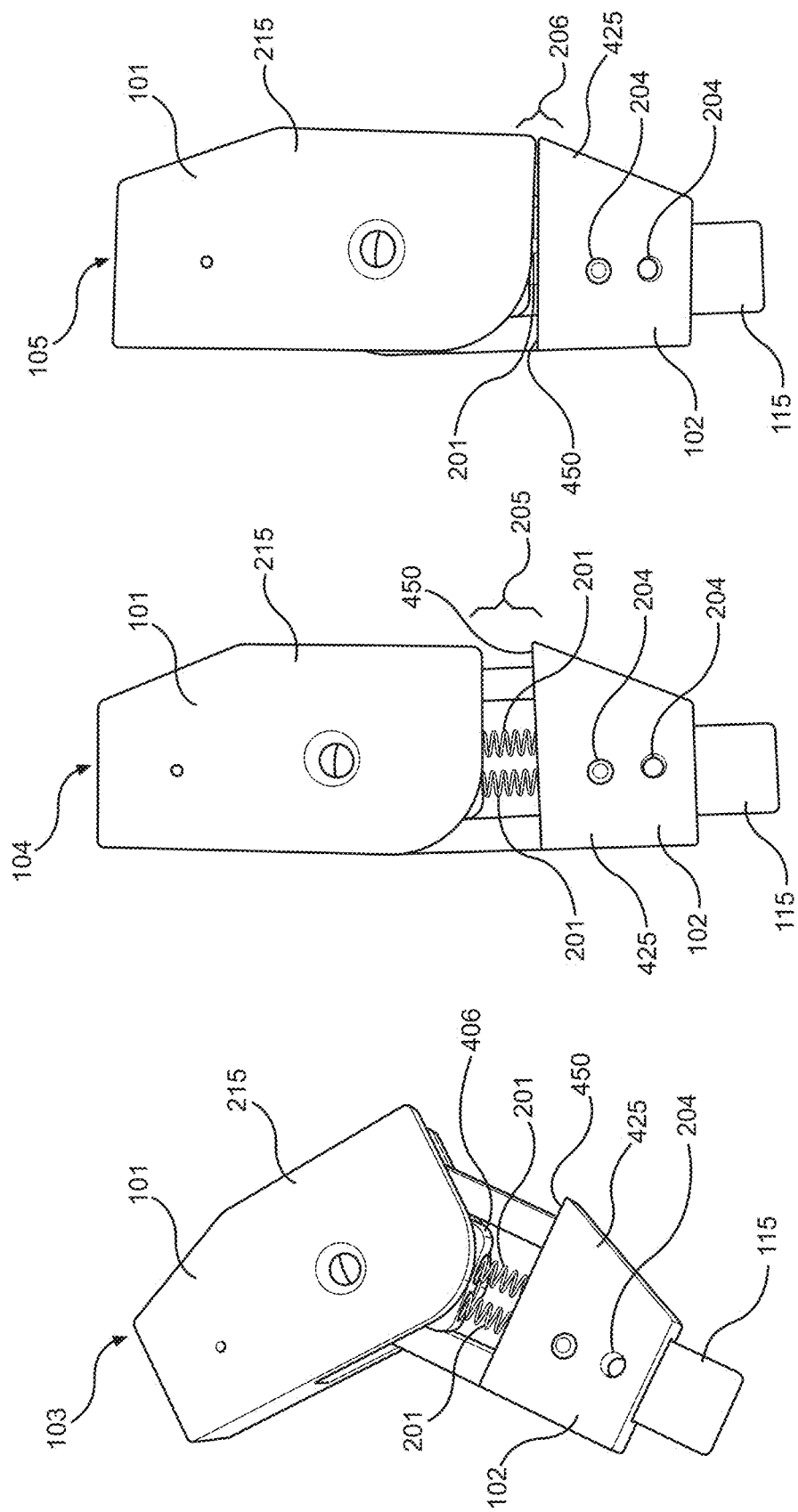

KNEE BRACE SPRING LOCK AND RELEASE HINGE

FIELD OF THE INVENTION

The present invention relates to knee brace hinges. In particular, the present invention relates to a lock and release rotational knee brace hinge.

BACKGROUND

The current state of the art only provides for a knee brace hinge that rotates, but does not lock in place when walking. Some provide a locking mechanism that requires a user to manually lock the hinge in place by hand. This becomes cumbersome for a user to use and does not simulate a true walking motion.

There exists a need in the art for an improved knee brace hinge that simulates a walking motion by locking into place when a user steps down. Likewise, it should unlock and rotate when a user releases weight from that leg. Therefore, there exists a need in the art for a knee brace spring lock and release hinge as claimed and described herein.

SUMMARY OF THE INVENTION

Embodiments of the present invention are related to a knee brace spring lock and release hinge including a first section and second section. The first section has an arched support housing with a J-curved recess. The second section includes a base with base platform, an arched support surrounding a rotational wheel, a wheel pad abutting a portion of the wheel, and at least one spring extending from the base platform to the wheel pad. The second section is structured to rotate within the J-curved recess when the at least one spring is extended. The second section is structured to be locked into place when the at least one spring is compressed.

In this embodiment, the first section and the second section may each include a brace support recess structured to receive a longitudinal brace support. The hinge may be structured to rotate between a vertically locked first position and at least a 90-degree angle second position and the arched support may include a first leg and a second leg. The hinge may be prevented from rotating when the second leg abuts a wall created by the J-curved recess when the at least one spring is compressed. Furthermore, a curved portion of the arched support may be structured to allow the second section to rotate within the J-curved recess when the at least one spring is extended. Additionally, the wheel may rotate along an axle and the axle may double as a fastener that connects the first section to the second section.

Another embodiment may include a knee brace spring lock and release hinge with a first section and second section. The first section may have an arched support housing with a recess formed by two generally perpendicular walls connected by a curved wall. The second section may include a base, an arched support surrounding a rotational wheel, a wheel pad connected to a portion of the rotational wheel, and a plurality of springs extending from the base to the wheel pad. The second section may be structured to rotate within the recess when the plurality of springs is extended. Also, the second section may be structured to be locked in place when the plurality of springs is compressed.

In this embodiment, the arched support may be structured to reduce rotational space within the recess when the plurality of springs is compressed, thereby preventing the second section from rotating. The hinge may be structured to be attached to a knee brace whereby the brace hinge is structured to lock when a user steps down with their weight on a leg with the brace and is structured to rotate when a user releases their body weight from that leg.

Furthermore, the wheel pad may include two spring pad holes structured to receive two springs therein. Likewise, the base may include a base platform with two spring base holes configured to receive two springs therein. The base may be angled on one side and straight on another side, and the wheel pad may be curved on a first side and flat on an opposing side. The plurality of springs may push the wheel pad distally from the base when extended and abut the wheel pad to the base when compressed. Additionally, an arched support curve atop the arched support may be flush with the rotational wheel when the plurality of springs is extended. It may be distal to the rotational wheel creating space therebetween when the plurality of springs is compressed.

Furthermore, a portion of the arched support curve atop the arched support may be pushed into the curved wall and a leg of the arched support may align with one of the perpendicular walls when the plurality of springs is compressed creating a second section wedge within the recess preventing rotation of the second section.

Another embodiment of the invention may include a knee brace spring lock and release hinge with a first section and a second section. The first section may include an arched support housing with a J-curved recess. The second section may include a base with base platform, an arched support surrounding a rotational wheel, a wheel pad connected to a portion of the rotational wheel, and at least one spring extending from the base platform to the wheel pad. It may have an axle permeated through a medial wheel sheath whereby the axle is a threaded fastener structured to secure the first section to the second section. The second section may be structured to rotate within the J-curved recess when the at least one spring is extended and it may be structured to be locked in place when the spring is compressed.

The hinge itself may be structured to be attached to a knee brace. It may be structured to lock when a user steps down with their body weight on a leg with the brace and may be structured to rotate when a user releases their body weight from that leg. Both the first section and the second section may include a brace support recess structured to receive a longitudinal brace support.

BRIEF DESCRIPTION OF THE DRAWINGS

FIG. 2A is a side perspective view of the knee brace spring lock and release hinge illustrated in FIG. 1A.

FIG. 2B is a side perspective view of the knee brace spring lock and release hinge illustrated in FIG. 1B.

FIG. 2C is a side perspective view of the knee brace spring lock and release hinge illustrated in FIG. 1C.

DETAILED DESCRIPTION OF THE INVENTION

The present invention will now be described in detail with reference to the accompanying drawings. The embodiment descriptions are illustrative and not intended to be limiting in any way. Other embodiments of the invention will readily suggest themselves to persons with ordinary skill in the art after having the benefit of this disclosure. Accordingly, the following embodiments are set forth without any loss of generality and without imposing limitation upon the claimed invention.

Directional terms such as "above" "below" "upper" "lower" and other like terms are used for the convenience of the reader in reference to the drawings. Additionally, the description may contain terminology to convey position, orientation, and direction without departing from the principles of the present invention. Such positional language should be taken in context of the represented drawings.

Quantitative terms such as "generally" "substantially" "mostly" and other like terms are used to mean that the referred object, characteristic, or quality constitutes a majority of the referenced subject. Likewise, use of the terms such as first and second do not necessarily designate a limitation of quantity. Such terms may be used as a method of describing the presence of at least one of the referenced elements or may provide a means of differentiating orientation. The meaning of any term within this description is dependent upon the context within which it is used, and the meaning may be expressly modified.

Figure 1A:
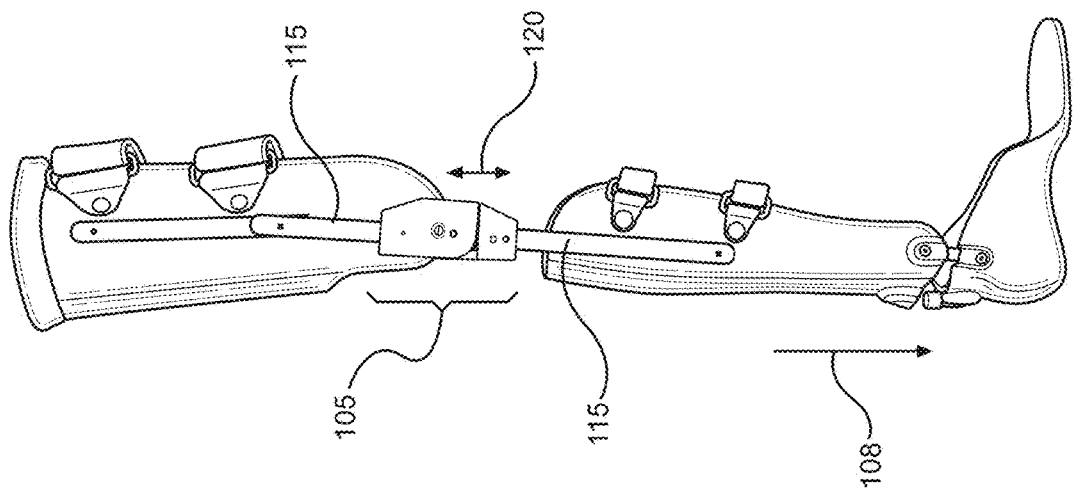
FIG. 1A is an environmental side view of the knee brace spring lock and release hinge in a bent orientation according to an embodiment of the invention.
Figure 1B:
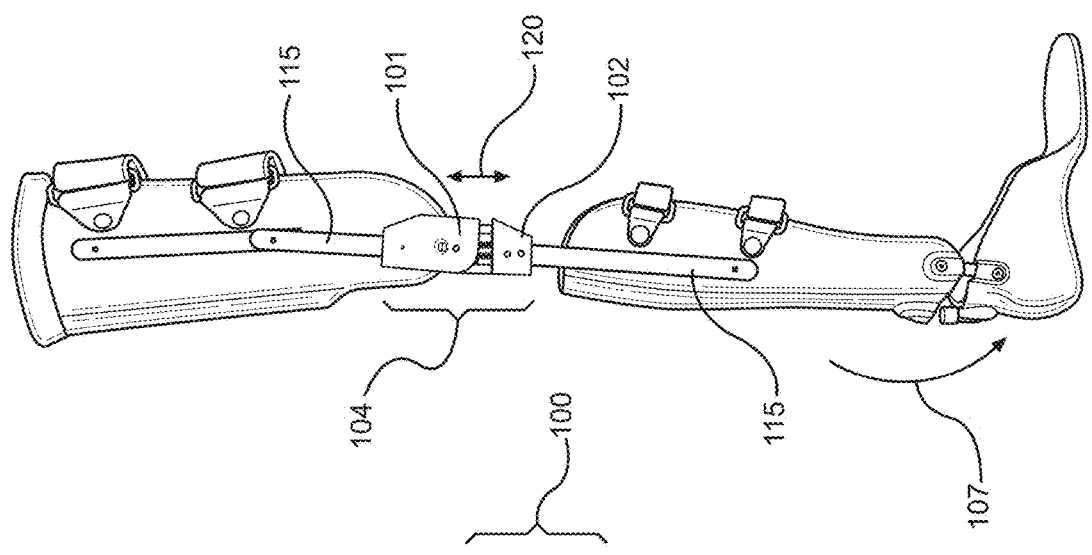
FIG. 1B is an environmental side view of the knee brace spring lock and release hinge illustrated in FIG. 1A in a straight unlocked orientation.
Figure 1C:
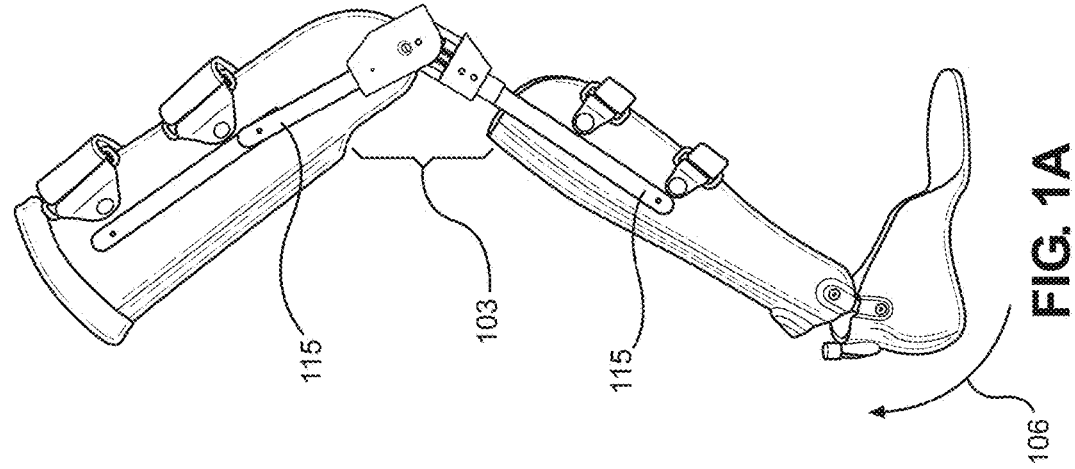
FIG. 1C is an environmental side view of the knee brace spring lock and release hinge illustrated in FIG. 1A in a straight locked orientation.

Referring now to FIGS. 1A, 1B, and 1C, a knee brace spring lock and release hinge 100, hereinafter hinge 100, will be described more fully. FIG. 1A illustrates the hinge 100 in a bent orientation 103 thereby bending the entire knee brace when a user has swung their leg backward 106 when walking. FIG. 1B illustrates the hinge 100 in a straight, but open and unlocked orientation 104. This may occur when a user has swung their leg forward, but has not yet stepped down with their weight on that leg 107. FIG. 1C illustrates the hinge 100 in a straight, closed and locked orientation 105. This may occur when a user has swung their leg forward and has applied weight to take a step forward 108.

The hinge 100 may include a first section 101 and a second section 102. The first section 101 and the second section may be attached to a knee brace via longitudinal support brace 115. Respective longitudinal support braces 115 may attach to the hinge 100 at an upper portion of the first section 101 and a lower portion of the second section 102.

As shown, when a user has swung their leg backwards 106, the first section 101 and second section 102 are separated allowing the hinge 100 to rotate freely backwards. However, a vertical spring motion 120 allows the hinge 100 to compress when a user has swung their leg forward and has taken a step using their weight on that leg.

FIGS. 2A, 2B, and 2C take a closer look at the operational features of the hinge 100. FIG. 2A illustrates the hinge 100 in a bent orientation 103. As shown, the first section 101 may include a first section exoskeleton 215 that encloses internal componentry.

One such internal component of the second section 102 may be a wheel pad 406. The wheel pad 406 may receive at least one spring 201. In this embodiment the wheel pad 406 receives a pair of springs 201. The springs 201 may be connected to the second section base 425 at an opposing end. The second section base 425 may include a base platform 450 with a flat ledge structured to act as a rotational stopper when meeting the first section exoskeleton 215 in a straight closed and locked orientation 105. The second section base 425 includes one angled side and an opposing straight side.

FIG. 2B shows the hinge 100 in a straight, open and unlocked orientation 104 whereby a user has rotated their leg forward but not stepped downward. Here, there may be a gap 205 between the first section 101 and the second section 102 because the springs are extended and separating the two.

FIG. 2C illustrates the hinge 100 in a straight, closed, and locked orientation 105 whereby a user has rotated their leg forward and stepped, applying their body weight downward. Therefore, there is no gap 206 between the first section 101 and the second section 102 because the springs 201 have been contracted. Hence, the first section 101 is abutting the second section 102 and the hinge 100 is unable to rotate further forward because of the locking features in this position.

Also shown in these figures is a brace support aperture 204 used to secure a longitudinal support brace 115 to the second section 102. A similar brace support aperture 204 is used to secure a longitudinal support brace 115 to the first section 101.

Figure 3:
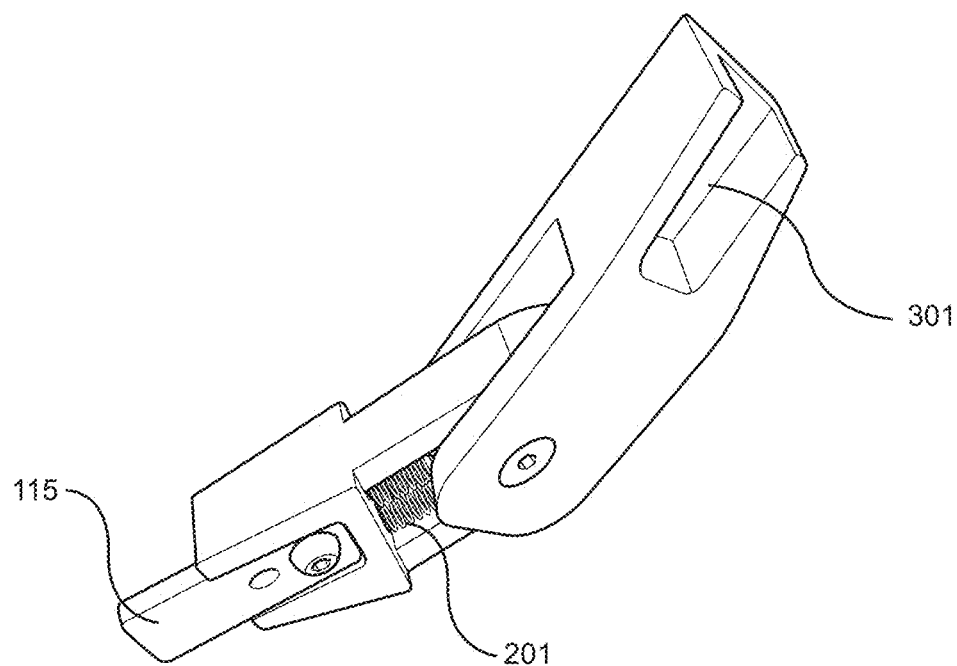
FIG. 3 is an overhead side perspective view of the knee brace spring lock and release hinge in FIG. 1A.

FIG. 3 is a rear view of an embodiment of the hinge 100 illustrating a brace support recess 301 capable of fitting therein a longitudinal support brace 115. Both the first section 101 and the second section include a brace support recess 301 therein whereby a respective longitudinal support brace 115 may be fitted thereto. As shown, the springs 201 may still be extended when the hinge 100 is in a bent orientation 103.

Figure 4:
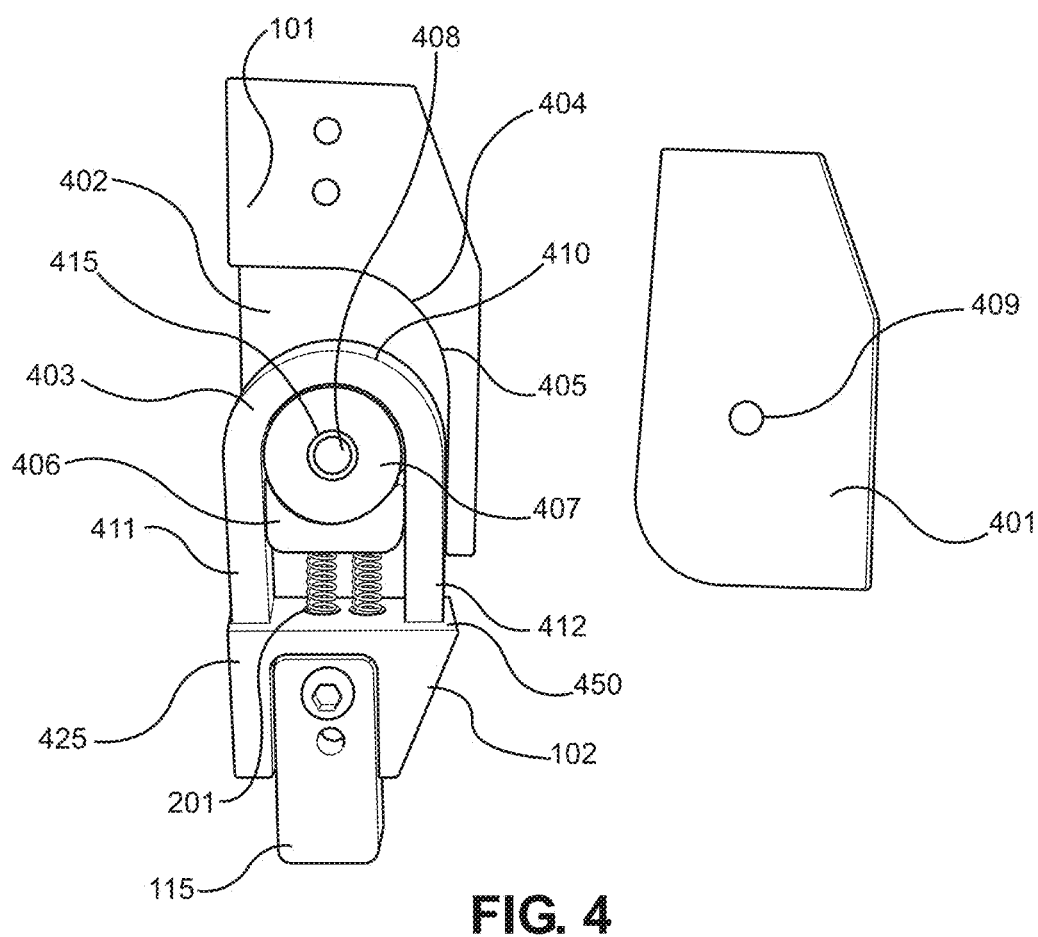
FIG. 4 is an internal side view of the knee brace spring lock and release hinge illustrated in FIG. 1A with cover plate removed.

FIG. 4 illustrates more internal componentry of the hinge 100 as a first section cover plate 401 has been removed. The first section cover plate 401 may include a threaded cover aperture 409 allowing it to be removably attached to the hinge 100 via the axle 408. The axle 408 may pass through both the first section 101 and the second section 102 securing one to the other and allowing rotation of the hinge 100 along its axis. The axle 408 itself may be threaded because it may serve the dual purpose of securing the first section cover plate 401 to the hinge 100 while also providing a rotational axis for the hinge 100. Therefore, the axle 408 may pass through an axle sheath 415, which may be a surrounding tube through a middle portion of the hinge 100 reducing friction that may occur from threading of the axle 408 and facilitating smooth rotation of the hinge 100.

As shown, the second section 102 may fit into the arched support housing 402 of the first section. The arched support housing 402 may include a j-curved notch or recess forming a j-curved wall 405. In some embodiments, this j-curved recess may be formed by two generally perpendicular walls connected by a curved wall. The recess may allow an arched support 403 from the second section 102 to fit and operate therein.

The second section 102 may include a second section base 425 with a second section base platform 450. The arched support 403 may be a rigid arch extending from one end of the base platform 450 proximate another. Therefore, the arched support 403 may include a first leg 411 and a second leg 412 on either side of an arch support curve 410. Within the arched support 403 may be a rotational wheel 407 including a medial aperture encapsulating the axle sheath 415 with axle 408 therein. In its straight, unlocked, orientation 104 the rotational wheel 407 may be abutted on the underside by the wheel pad 406. The wheel pad 406 may be curved on one end to geometrically conform to the curve of the wheel pad 406 to which it abuts. An opposing end of the wheel pad 406 may be flat so as to accommodate the springs 201 therein. As such, the springs 201 keep the curved portion of the wheel pad 406 flush with the rotational wheel 407 at all times since they push away from the base platform 450 at one end and toward the wheel pad 406 and rotational wheel 407 at the other. Likewise, the arch support curve 410 atop the arched support 403 may be flushed with the rotational wheel 407 when the springs 201 are extended, since they push the base platform 450 away from the rotational wheel 407 and the arch 410 of the arched support gets caught thereon. Furthermore, the arched support curve 410 atop the arched support 403 may be distal to the rotational wheel 407 creating space therebetween when the springs 201 are compressed. This pushes the arch support 403 into the housing walls 405 and forms a second section wedge preventing rotation of the second section 102.

Figure 5:
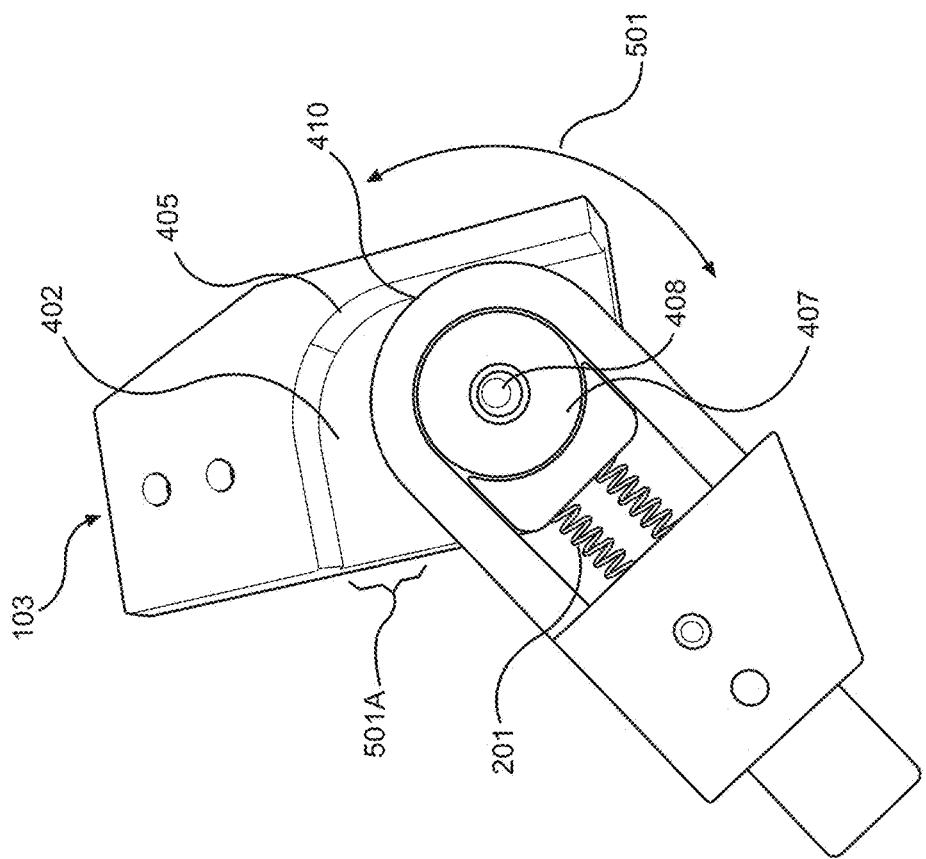
FIG. 5 is a side perspective view of the knee brace spring lock and release hinge illustrated in FIG. 1A.

FIG. 5 illustrates the internal componentry of the hinge 100 when it is in the bent orientation 103. As shown, when there is not downward pressure applied to the springs 201 and they are extended, the arched support curve 410 is biased away from the housing wall 405. Therefore, there exists space 501A for the arched support 403 to rotate 501 within the arched support housing 405. The rounded nature of the arched support curve 410 also facilitates rotation 501 since it is able to roll off of the housing wall 405. The second section 102 as a whole is able to rotate to at least a 90-degree orientation within the J-curve of the support housing 405 when the springs 201 are extended.

Figure 6:
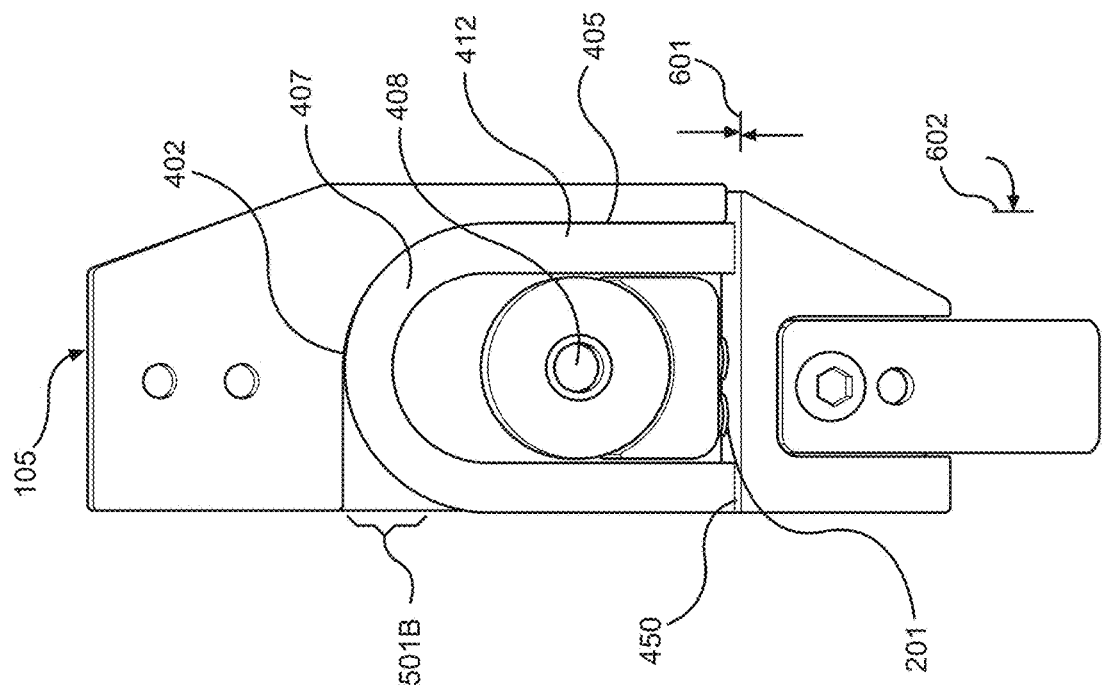
FIG. 6 is a side perspective view of the knee brace spring lock and release hinge illustrated in FIG. 1C.

FIG. 6 shows the internal componentry of the hinge 100 when in its vertical, closed, and locked orientation 105. As shown, there is downward pressure being applied to the hinge 100 as when a user has stepped with that leg. Therefore, the springs 201 are compressed and the wheel pad 406 is pressed against the base platform 450. This in turn, pushes the arched support 403 into the arched support housing walls 405 leaving little to no gap 501b between the two and thereby preventing the second section 102 from being able to rotate. Furthermore, in this position, the second leg 412 may abut the J-curved wall 405 further preventing rotation. Hence, the range of motion of the hinge 100 may be from a vertically locked position when the springs 201 are compressed, to at least a 90-degree angled second position when the springs 201 are extended. In other words, a portion of the arched support curve 410 atop the arched support 403 may be pushed into the housing curve 404 and a leg 412 of the arched support 403 may align with one of the perpendicular walls 405 when the plurality of springs 201 are compressed. This is what creates the second section 102 wedge within the housing recess 402 preventing rotation 602 of the second section 102.

Figure 7A:
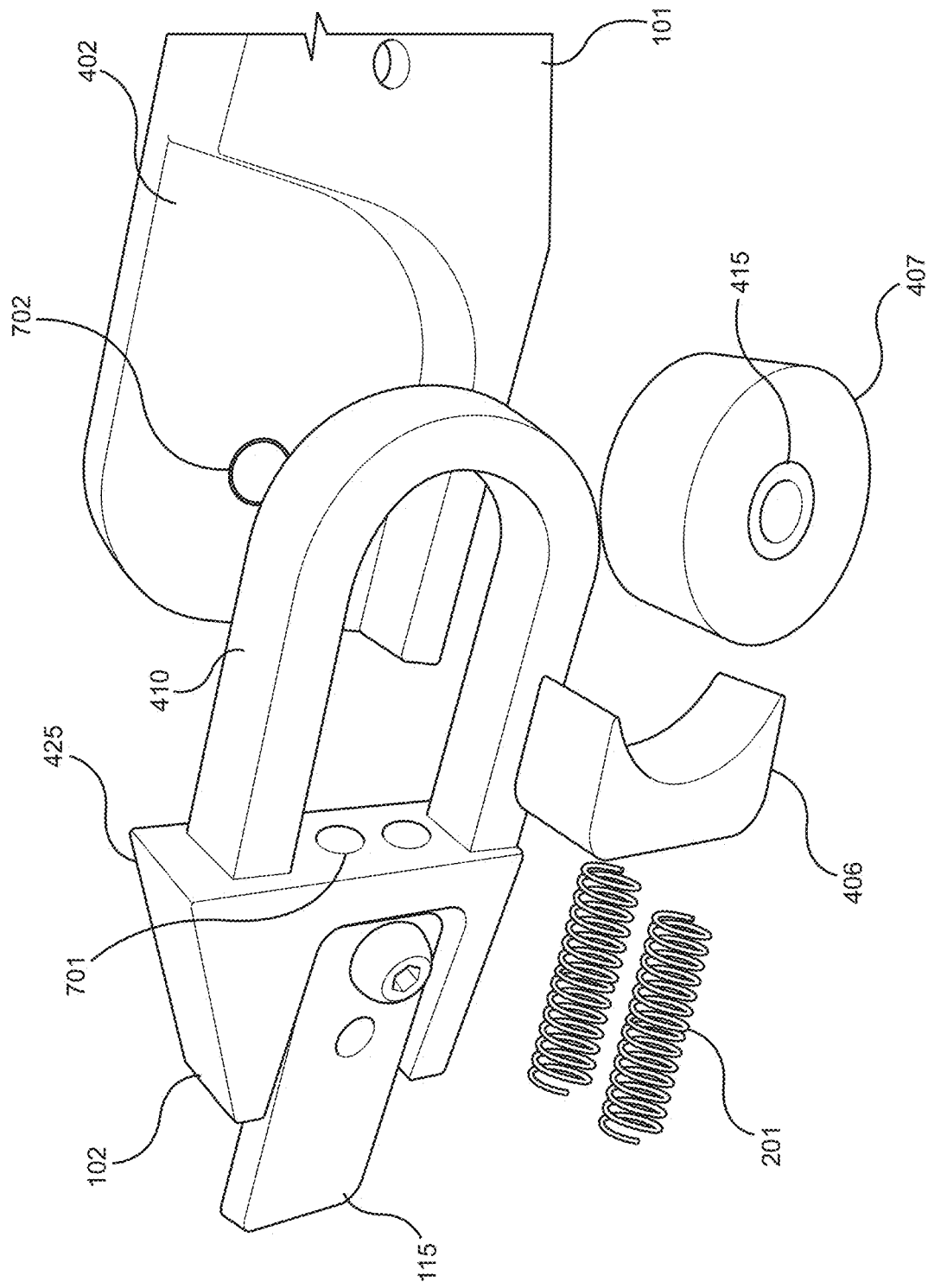
FIG. 7A is an exploded view of componentry of the knee brace spring lock and release hinge.

FIGS. 7A through 7E illustrate the componentry of the hinge 100 in more focused detail. FIG. 7A shows an exploded view of the internal componentry including the rotational wheel 407 and axle sheath 415. The wheel pad 406 and springs 201 are shown as well as a better view of the second section base 425 with spring base holes 701 illustrating how the springs 201 may fit therein to secure in place on the second section base platform 450. Also shown is how the arched support 410 connects to the second section base platform 450. Additionally, a different view of the first section 101 with its arched support housing 402 and housing aperture 701 are shown.

Figure 7B:
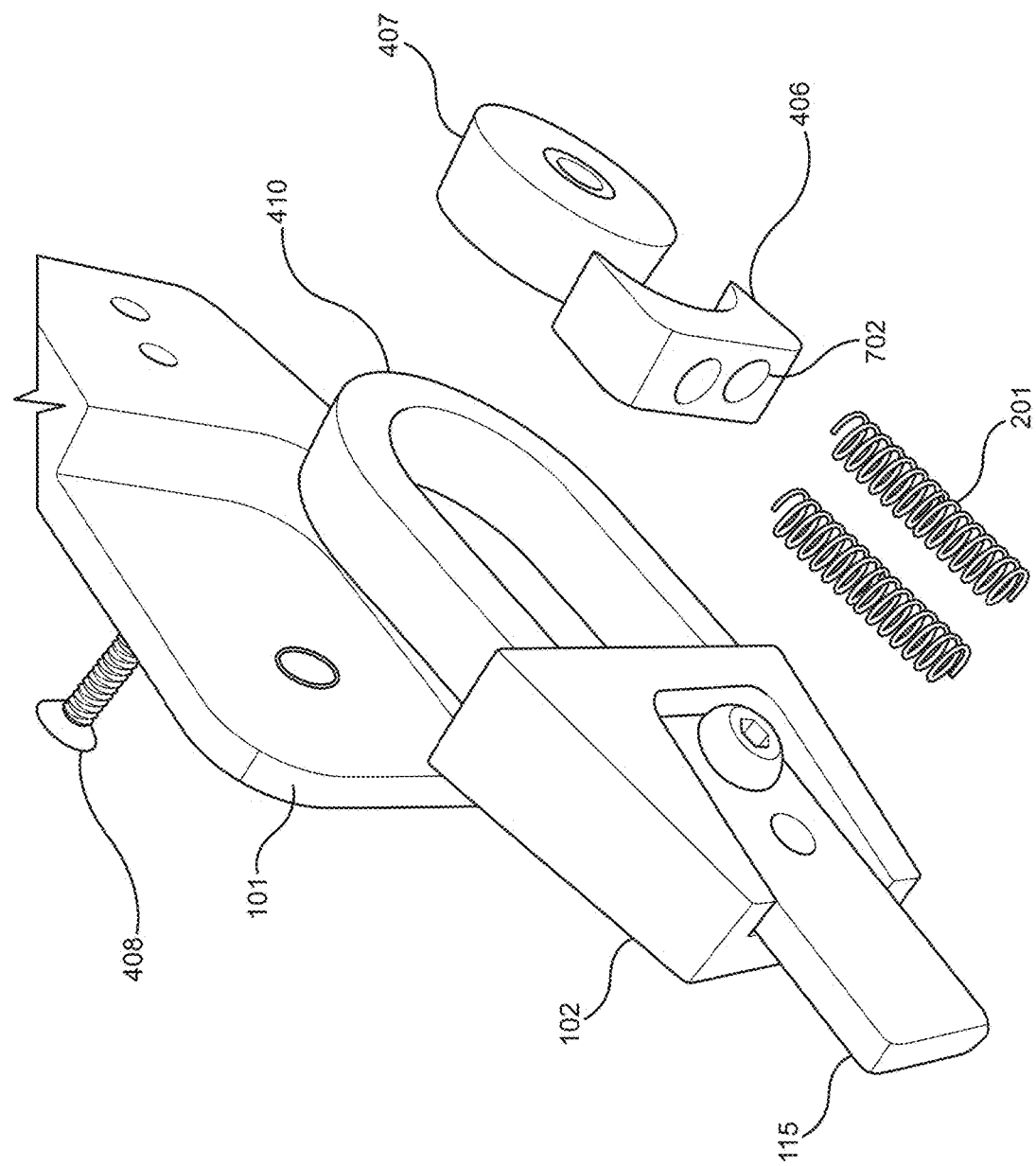
FIG. 7B is an exploded view of componentry of the knee brace spring lock and release hinge.
Figure 7C:
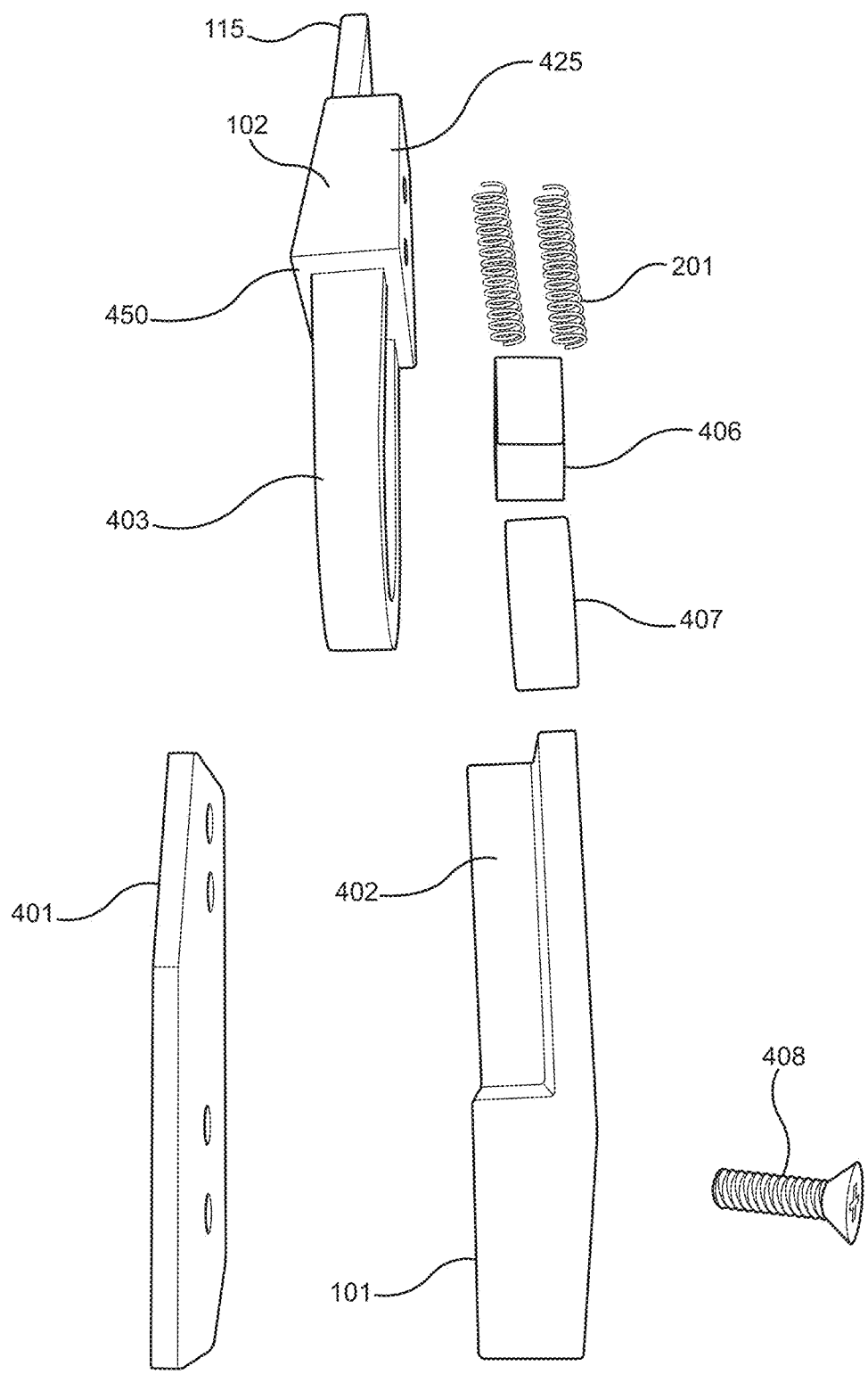
FIG. 7C is an exploded view of componentry of the knee brace spring lock and release hinge.

FIG. 7B illustrates an exploded view of the internal componentry from a different angle that shows the wheel pad 406 with spring pad holes 702 located on the flat portion thereof. The spring pad holes 702 may be designed to fit the springs 201 therein so that they may secure in place between there and the second section base platform 450. Also shown in this view is the axle 408, which may also serve as the apparatus fastener. Meaning, the axle 408 may be a bolt that extends through both the first section 101 and the second section 102 securing the two together, while also providing a rotational axis. FIG. 7C also shows the internal componentry from a different perspective.

Figure 7D:
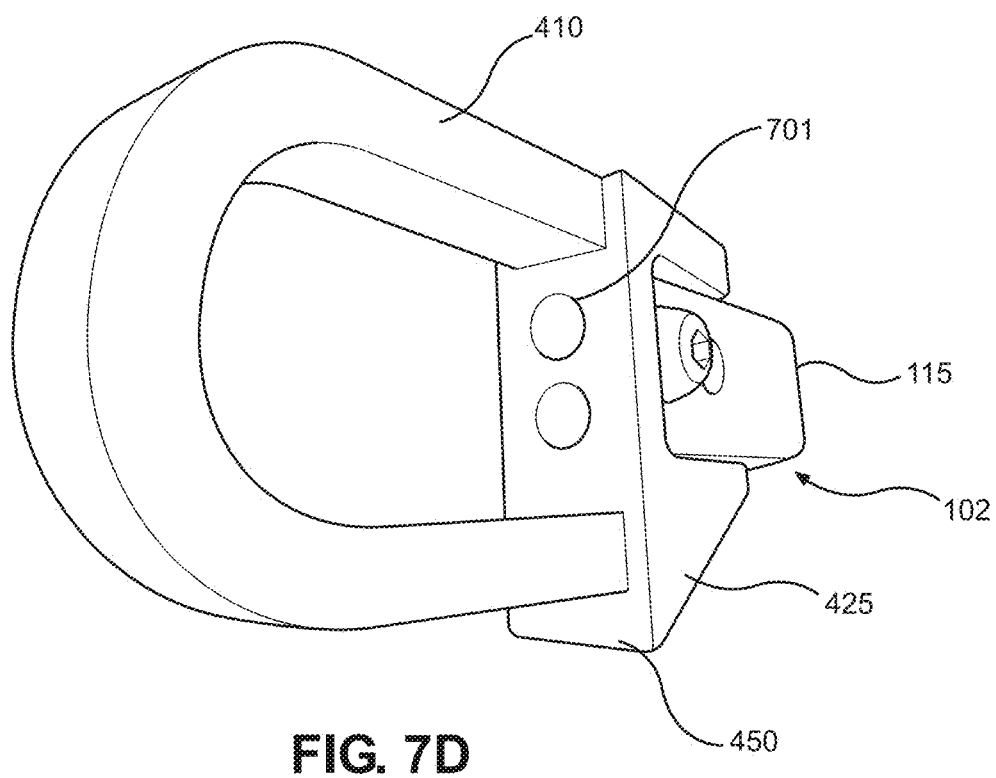
FIG. 7D is a top perspective view of a component of the knee brace spring lock and release hinge.
Figure 7E:
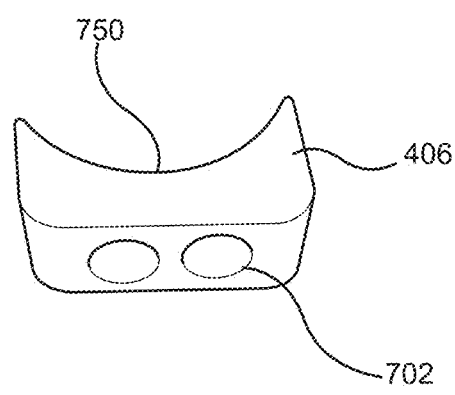
FIG. 7E is a bottom perspective view of a component of the knee brace spring lock and release hinge.

FIG. 7D shows the spring base holes 701 surrounded by the arched support 410 on the base platform 450. FIG. 7E gives a detailed view of the wheel pad 406 with its wheel pad curve 750 and spring pad holes 702. Again, the spring pad holes 702 are opposing the spring base holes 701 with the springs 201 fitted between the two to provide tensioned connectivity between the base platform 450, wheel pad 406, rotational wheel 407, arched support 403 and arched support housing 402 depending on orientation of the hinge 100 and applied force of the user.

That which is claimed is:

1. A knee brace spring lock and release hinge comprising:
    a first section comprising
        an arched support housing with a J-curved recess;
    a second section comprising
        a base with a base platform,
        an arched support surrounding a rotational wheel,
        a wheel pad abutting a portion of the rotational wheel, and
        at least one spring extending from the base platform to the wheel pad;
    wherein the second section is configured to rotate within the J-curved recess when the at least one spring is extended; and
    wherein the second section is configured to be locked into place when the at least one spring is compressed.

2. The knee brace spring lock and release hinge of claim 1 wherein the first section and the second section each include a brace support recess configured to receive a longitudinal brace support.

3. The knee brace spring lock and release hinge of claim 1 wherein the hinge is configured to rotate between a vertically locked first position and at least a 90-degree angle second position.

4. The knee brace spring lock and release hinge of claim 1 wherein the arched support includes a first leg and a second leg.

5. The knee brace spring lock and release hinge of claim 4 wherein the hinge is prevented from rotating when the second leg abuts a wall created by the J-curved recess when the at least one spring is compressed.

6. The knee brace spring lock and release hinge of claim 1 wherein a curved portion of the arched support is configured to allow the second section to rotate within the J-curved recess when the at least one spring is extended.

7. The knee brace spring lock and release hinge of claim 1 wherein the wheel rotates along an axle; and wherein the axle is a fastener that connects the first section to the second section.

8. A knee brace spring lock and release hinge comprising:
a first section comprising
an arched support housing with a recess formed by two generally perpendicular walls connected by a curved wall;
a second section comprising a base,
an arched support surrounding a rotational wheel,
a wheel pad connected to a portion of the rotational wheel, and
a plurality of springs extending from the base to the wheel pad;
wherein the second section is configured to rotate within the recess when the plurality of springs are extended;
wherein the second section is configured to be locked in place when the plurality of springs are compressed.

9. The knee brace spring lock and release hinge of claim 8 wherein the arched support is configured to reduce rotational space within the recess when the plurality of springs are compressed thereby preventing the second section from rotating.

10. The knee brace spring lock and release hinge of claim 8 wherein the hinge is configured to be attached to a knee brace; and wherein the brace hinge is configured to lock when the user steps down with their weight on a leg with the brace and is configured to rotate when a user releases their body weight from that leg.

11. The knee brace spring lock and release hinge of claim 8 wherein the wheel pad comprises two spring pad holes configured to receive two springs of the plurality of springs therein.

12. The knee brace spring lock and release hinge of claim 8 wherein the base includes a base platform with two spring base holes configured to receive two springs of the plurality of springs therein.

13. The knee brace spring lock and release hinge of claim 8 wherein the base is angled on one side and straight on another side.

14. The knee brace spring lock and release hinge of claim 8 wherein the wheel pad is curved on a first side and flat on an opposing side.

15. The knee brace spring lock and release hinge of claim 8 wherein the plurality of springs push the wheel pad distally from the base when extended and abut the wheel pad to the base when compressed.

16. The knee brace spring lock and release hinge of claim 8 wherein an arched support curve atop the arched support is flush with the rotational wheel when the plurality of springs are extended.

17. The knee brace spring lock and release hinge of claim 8 wherein an arched support curve atop the arched support is distal to the rotational wheel creating space therebetween when the plurality of springs are compressed.

18. The knee brace spring lock and release hinge of claim 8 wherein a portion of an arched support curve atop the arched support is pushed into the curved wall and a leg of the arched support aligns with one of the perpendicular walls when the plurality of springs are compressed creating a second section wedge within the recess preventing rotation of the second section.

19. A knee brace spring lock and release hinge comprising:
a first section comprising
an arched support housing with a J-curved recess;
a second section comprising
a base with a base platform,
an arched support surrounding a rotational wheel,
a wheel pad connected to a portion of the rotational wheel, and
at least one spring extending from the base platform to the wheel pad;
an axle permeated through a medial wheel sheath;
wherein the axle is a threaded fastener configured to secure the first section to the second section;
wherein the second section is configured to rotate within the J-curved recess when the at least one spring is extended;
wherein the second section is configured to be locked in place when the at least one spring is compressed;
wherein the hinge is configured to be attached to a knee brace; and
wherein the brace hinge is configured to lock when a user steps down with their body weight on a leg with the brace and is configured to rotate when the user releases their body weight from that leg.

20. The knee brace spring lock and release hinge of claim 17 wherein the first section and the second section each include a brace support recess configured to receive a longitudinal brace support.

* * * * *